US006731979B2

(12) United States Patent
MacDonald (10) Patent No.: US 6,731,979 B2
(45) Date of Patent: May 4, 2004

(54) PULSE WIDTH CARDIAC PACING APPARATUS

(75) Inventor: Stuart G. MacDonald, Pultneyville, NY (US)

(73) Assignee: Biophan Technologies Inc., West Henrietta, NY (US)

( * ) Notice: Subject to any disclaimer, the term of this patent is extended or adjusted under 35 U.S.C. 154(b) by 305 days.

(21) Appl. No.: 09/943,216

(22) Filed: Aug. 30, 2001

(65) Prior Publication Data

US 2003/0045907 A1 Mar. 6, 2003

(51) Int. Cl.[7] .............................................. A61N 1/362
(52) U.S. Cl. ........................................................... 607/9
(58) Field of Search .................. 600/508, 509, 600/515, 518, 373, 374, 377, 393; 607/4, 5, 7, 9, 11, 14, 15, 119, 122

(56) References Cited

U.S. PATENT DOCUMENTS

| | | | |
|---|---|---|---|
| 3,057,356 A | 10/1962 | Greatbatch |
| 3,478,746 A | 11/1969 | Greatbatch |
| 3,508,167 A | 4/1970 | Russell, Jr. |
| 3,669,095 A | 6/1972 | Kobayashi et al. |
| 3,686,958 A | 8/1972 | Porter et al. |
| 3,718,142 A | 2/1973 | Mulier |
| 3,789,667 A | 2/1974 | Porter et al. |
| 3,825,015 A | 7/1974 | Berkovits |
| 4,012,641 A | 3/1977 | Brickerd, Jr. et al. |
| 4,041,954 A | 8/1977 | Ohara |
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |
| 4,254,776 A | 3/1981 | Tanie et al. |
| 4,325,382 A | 4/1982 | Miodownik |

(List continued on next page.)

FOREIGN PATENT DOCUMENTS

WO     WO 01/74241     10/2001

OTHER PUBLICATIONS

A. Jerwzewski et al.;, "Development of an MRI–Compatible Catheter for Pacing the Heart: Initial In Vitro and In Vivo Results," JMRI, ISHRM (US), vol. 6 (No. 6), p. 948–949, (Jun. 14, 1996).

W. Moshage et al., "A Non–Magnetic, MRI Compatible Pacing Center for Clinical Application in Magnetocardiography," Biomedizinixche Technik Band, Erganzungsband (Germany), p. 162–163, (Jun. 14, 1990).

(List continued on next page.)

*Primary Examiner*—Jeffrey R. Jastrzab
*Assistant Examiner*—Frances P. Oropeza
(74) *Attorney, Agent, or Firm*—Howard J. Greenwald, P.C.

(57) ABSTRACT

A cardiac assist system containing a device for delivering a first pacing pulse from said system to a heart, for ceasing the delivery of said first pacing pulse to said heart, for sensing whether the heart is beating, and for delivering a second pacing pulse from said system to the heart. Each of the first pacing pulse and the second pacing pulse are delivered to the heart within a period of less than about 100 milliseconds, and has a voltage of from about 2 to about 5 volts direct current. The time between the delivery of the first pacing pulse and the second pacing pulse is at least about 1 microsecond. The first pacing pulse and the second pacing pulse are delivered to the heart at a frequency of from about 2 kiloherz to about 5 megahertz; and they each have a duration of from about 0.1 microseconds to about 500 milliseconds. The cardiac assist system also contains a device for varying the voltage and/or the frequency of each of the pacing pulses.

14 Claims, 7 Drawing Sheets

U.S. PATENT DOCUMENTS

| | | |
|---|---|---|
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | de LaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelton et al. |

| | | |
|---|---|---|
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Alled, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,367,984 B1 | 4/2002 | Stephenson et al. |
| 6,564,096 B2 * | 5/2003 | Mest .......................... 607/14 |

OTHER PUBLICATIONS

C. Roos, et al., "Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85–94.

Mark, B. M. Hofman; "MRI–Compatible Cardiac Pacing Catheter," JMRI; May/Jun. 1997; p. 612.

A. A. Damji et al., "RF Interference Suppression in a Cardiac Synchronization System Operating in High Magnetic Field NMR Imaging System," Magnetic Resonance Imaging, vol. 6, pp. 637–640, (1988).

Frank G. Shellock et al., "Burns Associated with the use of Monitoring Equipment during MR Procedures," JMRI, Jan.-.Feb. 1996; pp. 271–272.

J. Nyenhuis et al., "Heating Near Implanted Medical Devices by the MRI RF–Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1988, vol. 8#6; pp. 1338–1342.

J. Rod Gimbel et al., "Safe Performance of Magnetic Resonance," PACE; vol. 19; Jun. 1996; pp. 913–919.

National Library of Medicine; "Rapid Ventricular Pacing in a Pacemaker Patient Undergoing Magnetic Resonance Imaging," Pub Med; Pacing Clin Electrophysiol; Jun. 1998; pp. 1336–1339 J. M. Fontaine et al.

National Library of Medicine; "Effects of Magnetic Resonance Imaging on Cardiac Pacemakers and Electrodes," Pub Med; Am Heart J; (1997); pp. 1–11 Achenbach et al.

M. Kusumoto et al., "Cardiac Pacing for the Clinician," Lippincott Williams & Wilkins; (2001); Chapter 1, pp. 9, 12, 13, 18, 22, 24.

Donald Fink; "Electronic Engineering," Electronic Engineers Handbook; 2nd edition, Mcgraw Hill; (1982); Section 14; pp. 29–45.

X Luo et al., "Electromagnetic Interference Shielding Using Continuous Carbon–Fiber Carbon–Matrix and Polymer–Matrix Composites," Composites Part B: Engineering; (1999); pp. 227–231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p 161–163.

M. Konings et al., "Catheters and Guidewires in Inerventional MRI; Problems and Solutions," Medical Mundi; 45/1; Mar. (2001).

M. Konings; "Development of an MR–Safe Tracking Catheter with a Laser Driven Tip Coil," Journal of Magnetic Resonance Imaging 2001:13:131–135. c. 2001 Wiley–Liss, Inc.

Eywong et al., "An Optical System for Wireless Detuning of Parallel Resonant Circuits" Journal of Magnetic Resonance Imaging; (2000); vol. 12, pp. 632–638.

Bernd Nowak; "Taking Advantage of Sophisticated Pacemaker Diagnostics," Excerpta Medica; (1999); pp. 172D–179D.

Jose A. Jogler et al., "Interaction of a Commercial Heart Rate Monitor With Implanted Pacemakers," Excerpta Medica; (1999); pp. 790–792.

J. A. Pomposo et al., "Polypyrrole–based Conducting Hot Melt Adhesives for EMI Shielding Applications," Elsevier; Synthetic Metals 104; (1999); pp. 107–111.

K. Grattan et al., "Fiber Optic Sensor Technology: An Overview," Elsevier; Sensors and Actuators 82; (2000); pp. 40–61.

L. Rippert et al., "Optical and Acoustic Damage Detection in Laminated CFRP Composite Materials," Elsevier; Composites Science and Technology 60; (2000); pp. 2713–2724.

C. Strandman et al., "A Production Process of Silicon Sensor Elements for a Fiber–Optic Pressure Sensor," Elsevier; Sensors and Actuators A63; (1997); pp. 69–74.

D. Howard et al., "A Single–Fringe Etalon Silicon Pressure Transducer," Elsevier; Sensors and Actuators 86; (2000); pp. 21–25.

Dan Haronian, "Displacement Sensing Using Geometrical Modulation in Reflection Mode (GM–RM) of Coupled Optical Waveguides," J. Micromech. Microeng., (UK), (1998); pp. 323–326.

H. Ghafouri–Shiraz, "A Novel Distributed Feedback Laser Diode Structure foran Optical Wavelength Tuanble Filter," Semicond. Sci. Technol. 12: (UK) (1997); pp. 1161–1165.

L. Kasarian, "A New Optical Fiber Multiplexer for Distortion–Free Light Transfer in Multichannel Fiber Optic Sensor Systems," Elsevier; Sensors and Actuators 84; (2000); pp. 250–258.

X. Yan et al., "Electric Field Controlled 2x2 Bypass Exchange Photorefractive Switch," IOP Publishing; (UK) (1998), pp. 383–386.

E. Piener et al., "A Micromachined Vibration Sensor Based on the Control of Power Transmitted Between Optical Fibres," Elsevier; Sensors and Actuators A65: (1998) pp. 23–29.

D. Sun et al., "High Performance Unidirectional Electrooptic Modulator Based On Polymeric Highly Multi–Mode Waveguides," Elsevier; Optics & Laser Technology 30; (1998); 481–489.

Engin Molva; "Microchip Lasers and Their Applications In Optical Microsystems," Elsevier; Optical Materials 11; (1999); pp. 289–299.

J. Linares et al., "Theory and Design of an Integrated Optical Sensor Based on Planar Waveguiding Lenses," Elsevier; Optics Communications 180; (2000); pp. 29–36.

O. Parriaux et al., "Coupling Gratings as Waveguide Functional Elements," IOP Publishing; Pure Appl. Opt. 5; (1996); pp. 453–469.

E T Enikov et al., "Three–Dimensional Microfabrication for a Multi– Degree of Freedom Capacitive Force Sensor Using Fibre–Chip Coupling" IOP Publishing; (UK); J. Micromechl. Microeng. 10;(2000) pp. 492–497.

J. Holm et al., "Through–Etched Silicon Carriers for Passive Alighnment of Optical Fibers to Surface–Active Optoelectronic Components" Elsevier;Sensors and Actuators 82; (2000) pp. 245–248.

M. Kimura et al., "Vibration Sensor Using Optical–Fiber Catilever with Bulb–Lens" Elsevier; Sensors and Actuators A66; (2000) pp. 178–183.

Y. Mao et al., "Three–Stage Wavelength Converter Based on Cross–Grain Modulation in Semiconductor Optical Amplifiers"Elsevier; Optics Communications 167; (1999) pp. 57–66.

X. Hu et al., "Dynamically Induced Irreversibility: Light Amplification and Quantum Noise Reduction in a V–Type Three–Level System" IOP Publishing; J. Opt. B: Quantum Semiclass. Opt. 2; (UK) (2000); pp. 570–575.

Y. Yim et al., "Lithium Niobate Integrated–Optic Voltage Sensorwith Variable Sensing Ranges" Elsevier; Optics Communications 152; Jul. 1, 1998; pp. 225–228.

C. Lee et al., "Electromagnetic Interference Shilding Efficiency of Polyaniline Mixtures and Multilayer Films" Elsevier; Synthetic Metals 102; (1999) pp. 1346–1349.

Marc Desmulliez, "Optoelectronics–VLSI System Integration Technological Challenges" Elsevier; Materials Science and Engineering B74;(2000) pp. 269–275.

J. Zook et al., "Fiber–optic Vibration Sensor Baed on Frequency Modulation of Light–Excited Oscillators" Elsevier, Sensors and Actuators 83: (2000); pp. 270–276.

M. Reta–Hernandez et al., "Attenuation of Low Frequency Magnetic Fields Using Active Shielding" Electric Power Systems, Research 45; (1998);pp. 57–63.

C. Huang et al., "The EMI Shielding Effectiveness of PC/ABS/Nickel–Coated Carbon–Fibre Composites" Elsevier; European Polymer Journal 36: (2000) pp. 2727–2737.

M. Balucani et al., "Optical Link for DigitalTransmission Using Porou Silicon Light Emitting Diode" Elsevier; Journal of Non–Crystalline Solids 266–269; (2000) pp. 1238–1240.

D. Egelman et al., "Calcium Dynamics in the Extracellular Space of Mammalian Nerual Tissue" Biophysical Journal; vol. 76; Apr. 1999; pp. 1856–1867.

* cited by examiner

PULSE WIDTH CARDIAC PACING APPARATUS

FIELD OF THE INVENTION

A cardiac assist system for delivering a multiplicity of pacing pulses to a heart within a period of less than about 100 milliseconds, and for varying the properties of such pulses as the response of a heart to them varies.

BACKGROUND OF THE INVENTION

Cardiac assist devices, commonly referred to as pacemakers, comprise a wide range of functions but share a need to provide stimulus to the heart in order to initiate a heartbeat, to eliminate arrhythmia, or to defibrillate the heart. Traditional cardiac assist devices rely on electronic means to stimulate the heart and to monitor the presence of a normal or abnormal heartbeat. These devices typically use a battery as the source of electrical power, and much development effort has been expended in increased battery capacity and in improvements in the energy efficiency of the pacemaker systems. Further improvements in energy efficiency would benefit both the device manufacturer and the implant patient.

To the best of applicant's knowledge, none of the prior art cardiac assist devices provide means for achieving this efficiency goal. It is an object of this invention to provide a device for improving the energy efficiency of a cardiac assist device while simultaneously monitoring the response of a heart to such device and adjusting the output of such device in response to such monitoring.

Many prior art patents disclose means for sensing the response of a heart to the input from a pacemaker. Thus, e.g., by way of illustration and not limitation, U.S. Pat. No. 5,957,857 discloses an improved automatic sensing system for an implantable pacemaker in which the sensing threshold is automatically set to optimally sense the P-wave or R-wave while rejecting noise. The invention of this patent is limited to rather traditional noise filtering and rejection techniques, and addresses the need to sense heart function at a relatively low speed; on the order of the second beat interval of the heart. The entire disclosure of this United States patent is hereby incorporated by reference into this specification.

U.S. Pat. No. 6,144,881 similarly discloses means to improve the detection of evoked potential caused by the heartbeat, by selectively rejecting polarization potential that is a byproduct of the stimulating signal sent by the pacemaker. However, the invention of this patent also restricts the sensing of heartbeat, and the attendant problem of noise rejection to the period after the pacing signal has been sent to the heart. While this patent suggests more advanced nonlinear filtering techniques and adaptive response to changes in heart response to long term pacing, it still does not provide any means for detecting the response of the heart prior to the end of the pacing signal. The entire disclosure of this United States patent is hereby incorporated by reference into this specification.

U.S. Pat. No. 5,871,512 discloses the use of digital signal processing to detect specific signal artifacts sensed by a pacemaker and specifically relating to a movement of electrical potential in a negative direction. However, as with the foregoing inventions, this measurement and analysis is done during a period in time after the entire pacing signal to the heart has been terminated. The entire disclosure of this United States patent is hereby incorporated by reference into this specification.

U.S. Pat. No. 5,330,512 deals in similar fashion with the problem of measuring evoked potential caused by the heartbeat in the presence of much higher polarization potential in the cardiac tissues immediately disposed around the pacing electrodes. It farther suggests the use of an additional electrode in a manner that permits the pacemaker system to make measurements of the electrical activity of myocardial tissue that are less susceptible to the effects of polarization potential. However, as with the foregoing inventions, this patent restricts the application of this technique to a period typically three milliseconds following the pacing signal, which itself is typically about one millisecond in length. The entire disclosure of this United States patent is hereby incorporated by reference into this specification.

Thus, these U.S. Pat. Nos. 5,957,857, 6,144,881, 5,871,512, and 5,330,512 disclose improvements in sensing heart activity in an individual with an implanted pacemaker, but they operate in a frequency range that is consistent with the pacing signal (typically about 1 kilohertz) and with the heartbeat (typically about 1 hertz).

U.S. Pat. No. 5,782,880 discloses a low energy pacing waveform for an implantable pacemaker, and suggests the use of a waveform different from the square-wave used in many pacemaker devices. This patent further discloses a pacing signal that is shaped so as to provide adequate safety factor in reliably pacing the cardiac tissue but that reduces the energy required to do so. The entire disclosure of this patent is hereby incorporated into this specification.

Reference may also be had to texts dealing with the topic of cardiac pacing. Thus, e.g., a text entitled "Cardiac Pacing for the Clinician," edited by M. Kusumoto and N. Goldschlager, and published by Lippincott Williams & Wilkins, 2001, contains several chapter sections that deal with the physiology of cardiac pacing and sensing, and that describe the methods used by contemporary manufacturers in dealing with the issues described above. In chapter 1 on page 9 of this text, the typical safety factors employed by physicians are described; these are a 2:1 safety factor for pacing signal voltage and a 3:1 safety factor for pacing signal duration. The text further teaches that the energy dissipated in a pacing signal is directly proportional to the duration of the signal and to the square of the voltage of this signal. Thus, typical practice results in a pacing signal that is 12-fold higher than a signal that would be adequate to initiate the heartbeat. This 12-fold excess is intended to provide a very reliable pacing system, but it also results in unnecessary and chronic damage to cardiac tissue, and in the wastage of more than 90% of the energy available in the pacemaker battery.

The above text further describes, on pages 12 and 13, the nature of the evoked potential that results from the heartbeat itself, and describes both its typical magnitude (10 to 20 millivolts) and its typical slew rate (1 to 4 volts per second).

The text further describes, on pages 18 to 24, the typical electrode structure used in pacing the heart and in sensing heart activity electrically. There is specific discussion of the ongoing debate relating to unipolar versus bipolar pacing, employing the use of one or two electrodes external to the pacemaker case, respectively.

Furthermore, and again referring to the text "Cardiac Pacing for the Clinician," and specifically to FIG. 1.15 on page 22, it is disclosed that the stimulation threshold of the heart increases substantially after initial implantation and use. It is generally acknowledged that damage to sensitive cardiac tissues is one of the primary causes of this increase, which in requires higher pacing voltages and safety factors.

It is an object of this invention to provide a cardiac assist device which is substantially more energy efficient than prior art cardiac assist devices and which, additionally, modifies its output in response to changing conditions in a heart.

SUMMARY OF THE INVENTION

In accordance with this invention, there is provided a cardiac assist system containing a device for delivering a first pacing pulse from said system to a heart, for ceasing the delivery of said first pacing pulse to said heart, for sensing whether the heart is beating, and for delivering a second pacing pulse from said system to the heart. Each of the first pacing pulse and the second pacing pulse are delivered to the heart within a period of less than about 100 milliseconds, and each said pacing pulse has a voltage of from about 2 to about 5 volts direct current. The time between the delivery of the first pacing pulse and the second pacing pulse is at least about 1 microsecond. The first pacing pulse and the second pacing pulse are delivered to the heart at a frequency of from about 2 kilohertz to about 5 megahertz; and they each have a duration of from about 0.1 microseconds to about 500 milliseconds. The cardiac assist system also contains a device for varying the voltage and/or the frequency of each of the pacing pulses.

BRIEF DESCRIPTION OF THE DRAWINGS

The invention will be described by reference to the specification and to the following drawings, in which like numerals refer to like elements, and in which.

DESCRIPTION OF THE PREFERRED EMBODIMENT

The device of this invention can be used with any conventional cardiac assist device; these devices are often referred to as "pacemakers." Thus, by way of illustration, one may use such device with one or more of the pacemakers disclosed in U.S. Pat. Nos. 6,278,897, 6,278,894, 6,278,057, 6,277,107, 6,277,078 (system and method for monitoring a parameter associated with the performance of a heart), 6,275,734 (efficient generation of sensing signals in an implantable medical device), 6,275,732, 6,272,377, 6,270,831, 6,266,564, 6,263,246 (method and apparatus for communications with an implantable device), 6,263,242, 6,259,954, 6,258,087, 6,256,541, 6,254,632 (implantable medical device having protruding surface structures for drug delivery), 6,247,474 (audible sound communication from an implantable medical device), 6,246,910 (rate response active implantable medical device), 6,238,686, and the like. The entire disclosure of each of these United States patents is hereby incorporated by reference into this specification.

Figure 1:
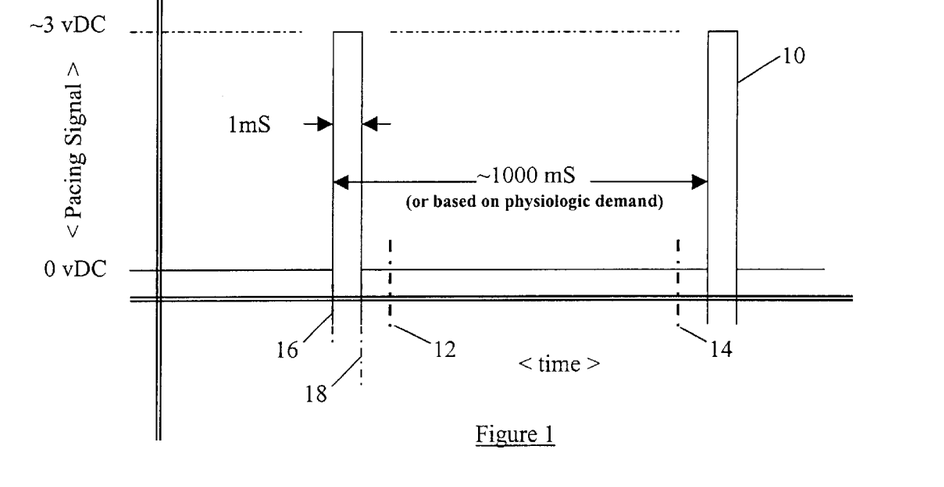
FIG. 1 is a graph depicting a typical pulse sequence used in pacing a human heart, over an interval equivalent to a nominal 1 Hz human heartbeat.

The output of a typical pacemaker is illustrated in FIG. 1, which is a graph of the electrical direct current voltage (vDC) applied to the electrode or electrodes at the distal end of a cardiac pacemaker lead, as a function of time. The indicated voltage of 3 vDC is a nominal value and is typically often selected by the physician based on the type of cardiac anomaly being corrected, the physical state of the patient's heart, and other factors. However, it should be understood that this value is intended to have a safety factor of two built into it; thus the typical voltage required to pace the heart is 1.5 volts direct current, or less.

Referring again to FIG. 1, and noting that the time axis is not to scale, the typical time between pacing events is nominally one second, or 1000 milliseconds (mS). In normal practice, using modem pacemakers, this time interval is not fixed but is variable based upon two factors. The first factor is whether or not the heart requires pacing in order to beat. The term 'demand pacemaker' applies to a device that senses heart activity electrically and does not send a pacing signal to the electrodes if the heart is beating on its own in a manner determined to be acceptable by the computer controller within the device, and based upon input programmed by the physician. Thus, during the time after the refractory period associated with the previous heartbeat ends 12, and up to a time when the next heartbeat is required 14, the pacemaker electrode is used to sense heart activity and to disable the next pacing signal 10 if the heartbeat is regular.

The second factor associated with demand pacing is physiologic demand; modem pacemakers are designed with additional sensing and analytical capability that permits the device to monitor physiologic demand associated with physical activity or other forms of stress that would result in an elevated heartbeat in a normal human subject. In response to this heightened physiologic demand, the pacing signal 10 would be generated at an earlier time than the 1000 mS delay indicated in FIG. 1.

Figure 2:
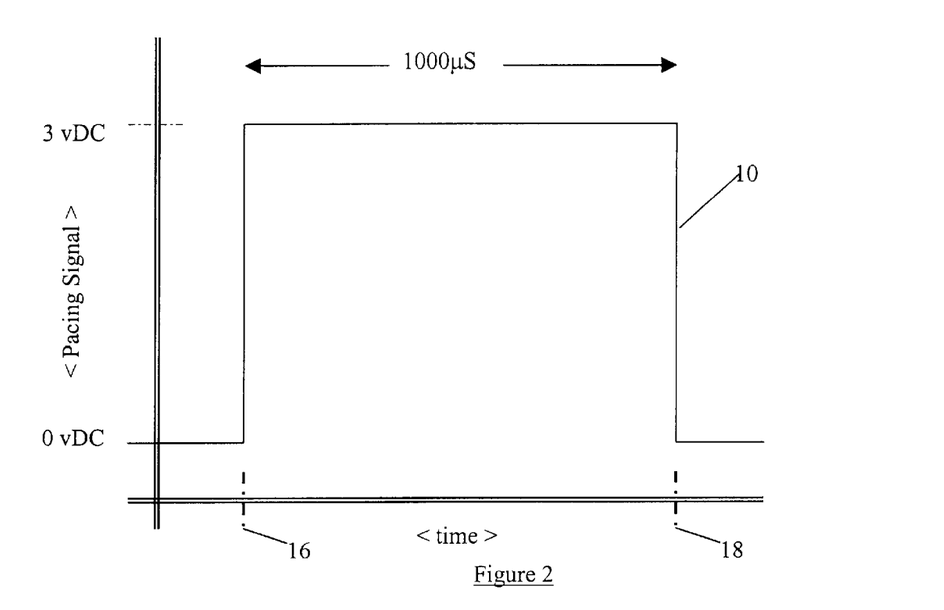
FIG. 2 is a similar graph depicting the pacing pulse as shown in FIG. 1, but with a much finer time scale.

FIG. 2 is an expanded view similar to FIG. 1, showing the pacing signal 10 over the nominal one-millisecond time interval of the actual pacing signal. The beginning of the pacing signal 16 and the end of the pacing signal 18 are shown in both FIG. 1 and FIG. 2 for reference. Note that there is no other activity in this one millisecond time interval; more particularly there is no attempt to sense heart activity nor the heart's response to the pacing signal during the time pacing time interval between times 16 and 18. This is in part due to the fact that while a relatively modest voltage (about 3 volts) is being applied to the heart cardiac tissue by the electrodes, the voltages sensed by the pacemaker in monitoring heart activity (typically in the millivolt range) would be unmeasurable using traditional techniques. In addition, the tissues surrounding the pacing electrode develop a polarization potential in response to the energy in the pacing signal; this serves to make measurements of heart activity via those same electrodes very difficult using traditional techniques. However, the interval between times 16 and 18 is very long in the context of modem computational electronic devices.

Figure 3:
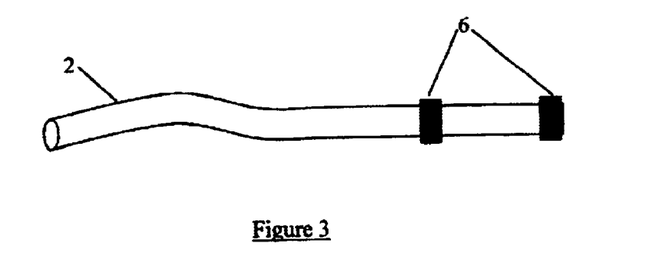
FIG. 3 is a schematic representation of a cardiac pacing lead with two electrodes.
Figure 4:
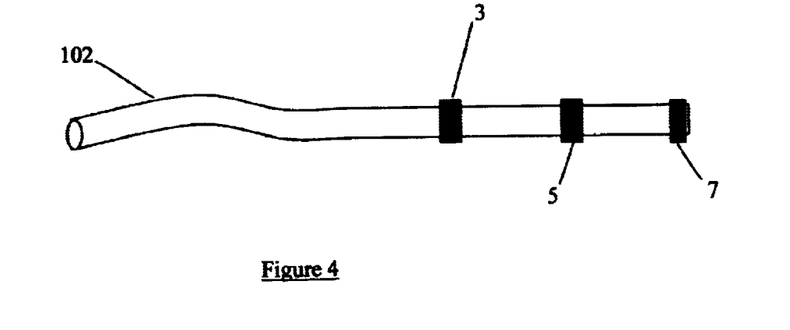
FIG. 4 is a schematic representation of a similar cardiac pacing lead with three electrodes.
Figure 5:
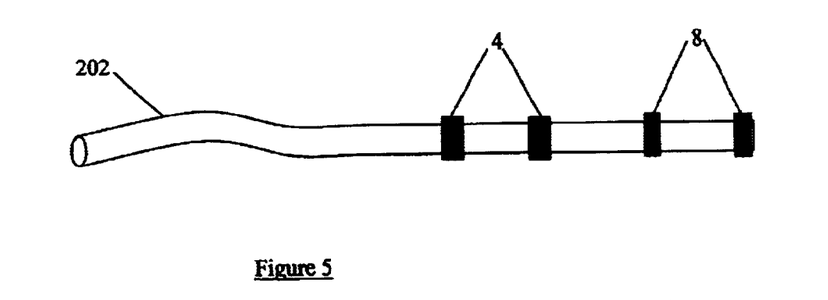
FIG. 5 is a schematic representation of yet another cardiac pacing lead with two pairs of electrodes.

FIGS. 3, 4, and 5 are schematic representations of a cardiac pacemaker lead 2 having various electrode configurations. In one preferred embodiment, and referring to FIG. 3, pacemaker lead 2 comprises one or more electrical conductors communicating from a connector on the body of the pacemaker device (not shown) to the electrodes 6 that are affixed by one of a number of techniques to the sensitive cardiac tissue that initiates the natural heartbeat and that is paced when necessary by the implanted pacemaker system. The configuration shown in FIG. 3 is for a bipolar pacemaker; the positive and negative terminals for electron flow through the cardiac tissue are the two electrodes 6. It should be noted that there is an alternative configuration referred to as unipolar, and it is not shown in this figure. In the case of a unipolar configuration, there is a single electrode 6 at the heart; the return path for electron flow is through the general bulk tissue back to the case of the device itself. In either unipolar or bipolar configurations, electrodes 6 are used both to pace the heart during the period between times 16 and 18 shown in FIGS. 1 and 2, but are also used to sense heart activity electrically between times 12 and 14 shown in FIG. 1.

In the embodiment depicted in FIG. 4, sensing electrode 7 is disposed at a distance of at least about 5 millimeters from pacing electrode 3 in order to provide a degree of electrical isolation between tissues that will develop a polarization potential and tissues being sensed for heartbeat activity. Similarly, in the embodiment depicted in FIG. 5, sensing electrode pair 8 is disposed at a distance of at least about 5 millimeters from pacing electrode pair 4.

In another preferred embodiment, cardiac pacemaker lead 2 is not an electrical conductor but rather comprises one or more optical fibers that carry light energy between the pacemaker device case and the electrodes 6. This embodiment may be used in order to create pacemaker leads that are immune to the intense radio frequency and magnetic fields associated with magnetic resonance imaging (MRI) and which fields can in some cases result in damage to the pacemaker and/or injury or death to the pacemaker patient who inadvertently undergoes MRI diagnosis. In this embodiment electrodes 6 are more complex than in the former embodiment; for purposes of pacing they comprise a photodiode (not shown) used to convert light energy to electrical energy within them, and in the case of sensing cardiac activity they also comprise a miniature electrical amplifier and light emitting diode source that creates an optical signal that travels from the electrode 6 back to a pacemaker device that uses the photonic catheter of this embodiment.

In one embodiment, the pacemaker device is similar to the MRI-compatible implantable cardiac pacemaker described in a commonly-owned patent application filed on or about May 24, 2001 as U.S. Ser. No. 09/865,049 in the names of Victor Miller, Wilson Greatbatch, Patrick Connelly, and Michael Weiner, for "MRI-COMPATIBLE PACEMAKER WITH POWER CARRYING PHOTONIC CATHETHER AND ISOLATED PULSE GENERATING ELECTRONICS PROVIDING VOO FUNCTIONALITY." The entire disclosure of this commonly owned patent application is hereby incorporated by reference into this patent application.

The Ser. No. 09/865,049 application describes a "V00 pacemaker," which, as is known to those skilled in the art, is asynchronous, having no feedback signal from the heart. By comparison, the pacemaker of the instant invention uses components and circuitry similar in nature to those described in the Ser. No. 09/865,049 application but for purposes of transducing pacing signals to the heart and transducing sensing signals from the heart.

Thus, by way of illustration, one may utilize the photonic catheter components illustrated in FIGS. 2 and 2A of the Ser. No. 09/865,049 application (see, e.g., the description of these components at pages 11, 12, and 13 of such case).

Thus, by way of further illustration, one may utilize the pulsed signal generator circuits illustrated in FIGS. 4 and 5 of the Ser. No. 09/865, 049 application (see, e.g., the description of these circuits at pages 13, 14, and 15 of such case).

Thus, e.g., the device disclosed in U.S. Pat. No. 5,454,837 might advantageously utilize the instant invention. Such patent claims a medical system for implantation in a body containing body tissue comprising: an implantable housing containing therapy-generating means for generating electrical signals; an implantable optical conductor having a first end and a second end; means for attaching said first end of said optical conductor to said therapy-generating means; implantable electrical means for in vivo electrically interacting with said body tissue; means for attaching said electrical means to said second end of said optical conductor; first converter means disposed at said first end of said optical conductor for converting said electrical signals into corresponding optical signals, said optical signals being transmitted by said optical conductor to said second end of said optical conductor; and second converter means disposed at said second end of said optical conductor for converting said optical signals into corresponding electrical signals supplied to said electrical means. The entire disclosure of this United States patent is hereby incorporated by reference into this specification.

In another embodiment, and referring to FIG. 4, the pacemaker lead 102 connects the pacemaker device case (not shown) to a set of electrodes 3, 5, and 7 at its distal end and affixed to cardiac tissue as in the previous embodiment. Electrode 5, as in the previous embodiment, is capable of either pacing the heart or sensing heart activity electrically. Electrode 3 is used only to pace the heart, and is identical in its function to that part of the function of the dual-purpose electrode 5. In like manner electrode 7 is used only for sensing heart activity electrically, in a fashion identical to that part of the function of the dual-purpose electrode 5. The reason for the configuration shown in FIG. 4 is that the cardiac tissue immediately involved in the pacing event, and which develops a polarization potential as a result of the pacing signal, is somewhat removed physically from the cardiac tissue immediately around the sensing electrode 7, thus providing some degree of isolation from polarization potential in the area where cardiac sensing is being done, but still providing ample opportunity for sensing any cardiac activity. Thus this embodiment provides the opportunity for sensing measurements to be made during dwell periods in the overall pacing signal wherein no voltage is being applied to the cardiac tissue.

In a further embodiment, and still referring to FIG. 4, pacemaker lead 102 does not contain electrical conductors but rather comprises one or more optical fibers, as described in a previous embodiment. Likewise, electrodes 3 and 5 have the capability to convert optical energy to electrical energy in order to pace the heart, and electrodes 5 and 7 comprise electrical amplifier and electricity-to-light conversion, as is also described in the previous embodiment.

In yet another preferred embodiment, shown in FIG. 5, pacemaker lead 202 connects the pacemaker device case (not shown) to a set of electrodes 4 and 8 at its distal end and is affixed to cardiac tissue as in the previous embodiments. In this embodiment, additional separation between the volume of cardiac tissue being paced (between electrodes 4) and the volume of cardiac tissue being sensed (between electrodes 8) is created in order to provide further improvements in electrical isolation between those areas, thereby providing further improvement in the ability to make sensing measurements during cardiac pacing.

In yet another embodiment, and still referring to FIG. 5, pacemaker lead 202 does not contain electrical conductors but rather one or more optical fibers, as described in a previous embodiment. Likewise, electrodes 4 have the capability to convert optical energy to electrical energy in order to pace the heart, and electrodes 8 comprise electrical amplifier and electricity-to-light conversion as also described in previous embodiments.

Figure 6:
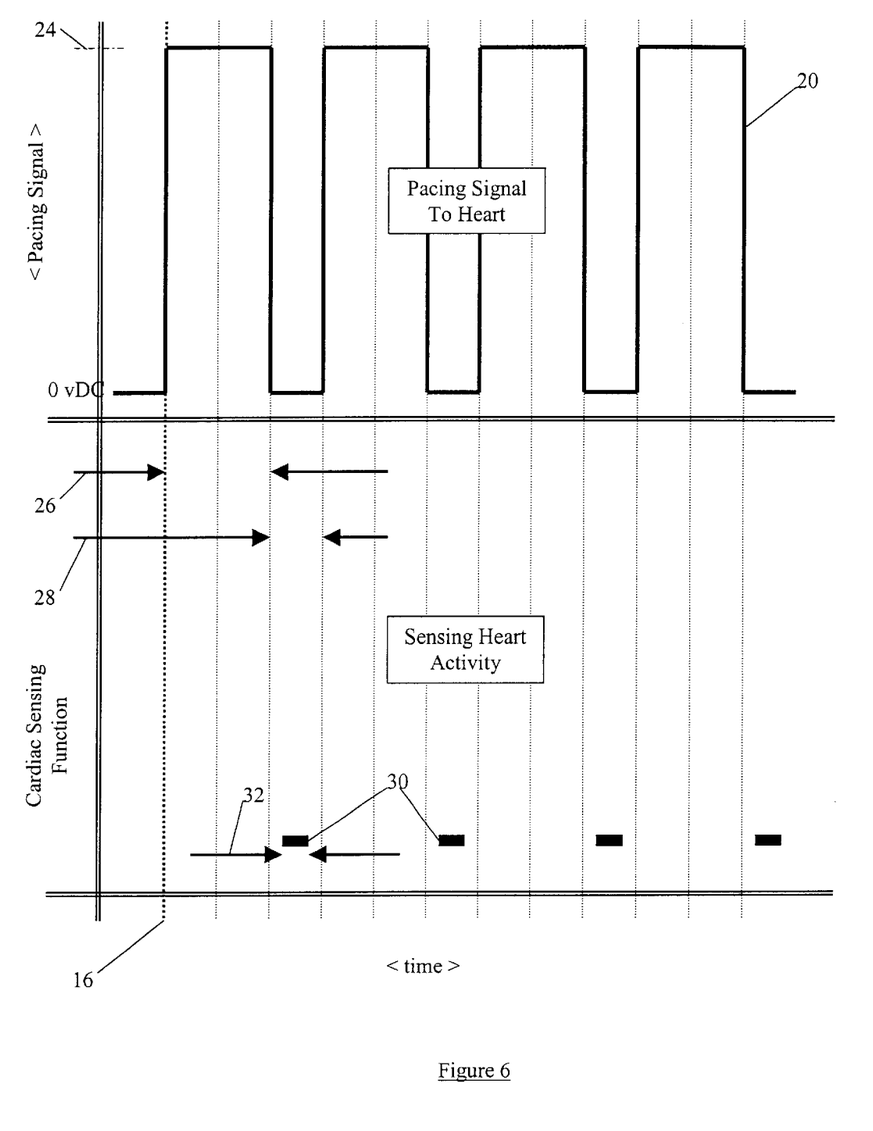
FIG. 6 is a graph depicting the use of pulsewidth pacing signals and interleaved periods for sensing heart activity.

In one preferred embodiment of this invention, a technique of pulsewidth modulation is used to pace the heart and to provide the opportunity for real-time measurement of cardiac tissue activity. Referring to FIG. 6 it may be seen that a pacing signal 20 that begins at time 16 is not a traditional square wave pulse as shown in FIGS. 1 and 2, but is a series of much faster pulses that apply a voltage 24 for a time period 26 and that apply no voltage during time period 28. For example, if time period 26 is chosen to be two microseconds and if time period 28 is chosen to be one microsecond, a single repeat of sequence 26 and 28 has a duration of three microseconds. If this sequence is repeated 333 times, the time interval for pulse 20 will be about one millisecond, corresponding to the time interval of a single traditional pacing signal to the heart. For purposes of this illustrative example and again referring to FIG. 6, voltage 24 may be chosen to compensate for the fact that no voltage is applied for one third of the time. In order for a pulsewidth signal 20 having the 66 percent duty cycle as described in this illustration to deliver the same amount of electrical energy to the cardiac tissue as in a square wave 3 volt d.c. pulse of 1 millisecond duration, and taking into consideration the relationship of energy to voltage in a purely resistive medium (energy is proportional to the square of the applied voltage), the voltage 24 will be chosen to be 3 volts d.c. multiplied by the square root of 1.5, or 3.67 volts direct current. If the frequency of pulsewidth modulated pacing curve 20 is high with respect to the reaction time of cardiac tissue, that tissue will react in the same manner to the pulsewidth modulated signal having 66 percent duty cycle and 3.67 volt peak signal level as it would to a square wave of the same duration at 3.0 volt.

The foregoing example is intended to be illustrative only; in the embodiment depicted, time periods 26 and 28 may range from below 1 microseconds to over 100 microseconds in order to optimize the response of the system to design choices in the pacemaker device or the pacemaker lead and electrodes. In addition, this embodiment provides for time periods 26 and 28 to be variable over time, both in absolute duration and in their ratio. Further, the applied voltage 24 may be variable over time within a single pacing signal 20, or between pacing signals, as a function of changes in physiologic demand or based on changes in programmed response of the pacemaker system. For purposes of this specification, the overall signal that spans between time 16 and time 18 will be referred to as the pacing signal, the shorter signals sent to the heart in multiples will be referred to as pulses, and the much shorter signals described in this illustrative example as having time duration 26 will be referred to as micropulses.

Referring once again to FIG. 6, it may be seen that a cardiac tissue sensing measurement 30 may be carried out during time period 32. In one embodiment of this invention, time period 32 may occur any time during the pacing signal and may have any duration appropriate to making said sensing measurement. In a preferred embodiment of this invention, time period 32 is selected to be shorter in duration than time period 28, and is further synchronized so as to fall within time period 28. The result is that the electrical measurement of cardiac tissue activity is done during a time period wherein there is not pacing signal applied to the tissue.

Referring again briefly to FIGS. 3, 4, and 5, it may be seen that in combination with the placement of electrodes 3, 4, 5, 6, 7, and 8 on pacemaker lead 2, 102 and 202 that provides isolation between the tissue being paced and the tissue being sensed, the additional temporal isolation of sensing period 32 from the active time period 26 of the pulsewidth modulated pacing signal 20, a means is provided to measure the onset of cardiac response to the pacing signal while said signal is still being generated as a set of multiple shorter pulses.

Figure 7:
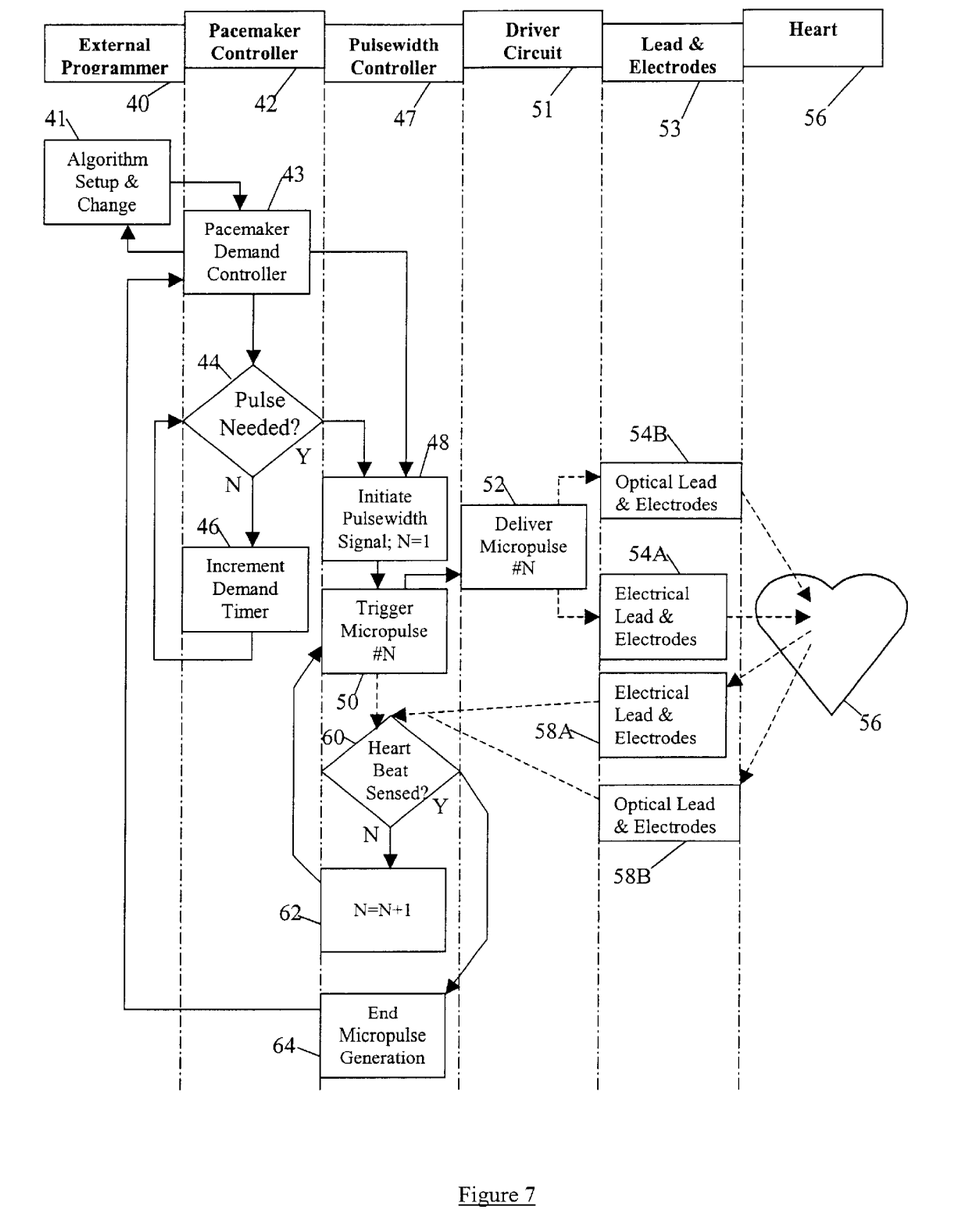
FIG. 7 is a flowchart depicting the process used to monitor cardiac tissue response to pacing signal and to provide real-time control of the pacing signal.

FIG. 7 is a flowchart depicting the process used to pace the heart with the aforementioned pulsewidth technique, to monitor the response of the cardiac tissue during the pacing pulse, and to end the pacing pulse when the heart has initiated a beat. This specification describes the process that would be used in a pacemaker typically referred to as a demand pacemaker. Further detail regarding this type of pacemaker may be found in Chapter 3 of the previously cited text "Cardiac Pacing for the Clinician." However, the invention described herein, and in particular the process depicted in the flowchart of FIG. 7, may be applied to all forms of pacemakers in current use.

Referring to FIG. 7, external programmer 40 communicates with the pacemaker control computer 42 via any of a number of techniques, including but not limited to radio frequency, magnetic, acoustic, near infrared light. One of the functions of the external programmer 40 is the initial setup conditions for the control algorithm 41; these are chosen by the physician, for the specific patient, based upon said patient's physical condition, the specific cardiac abnormality being treated, and other factors such as age, gender, and the like. Another function of programmer 40 is to adjust control algorithm 41 at later times depending upon changes in the patent's condition, or based upon feedback received from the pacemaker; in either case the physician may direct these changes or they may be designed into the software resident in external programmer 40.

Pacemaker controller 42 has as one of its functions the control of the pacing of the heart based upon physiologic demand. For purposes of this specification, the simplifying assumption will be made that pacemaker controller 42 monitors the patient's physiologic state and directs demand controller 43 to pace the heart at a rate determined by an algorithm residing in pacemaker controller 42. Thus the function of demand controller 43 is simply to monitor the heart during the period between times 12 and 14 from FIG. 1 and if the heart does not initiate a heart beat within that interval, the pacemaker then initiates a pacing signal, typically about 3 volts and having a duration of about 1 millisecond, via a standard lead and electrodes. Demand pacemakers and other cardiac assist devices not practicing the instant invention receive feedback information from the heart only in the interval between beats, so the logical function shown in FIG. 7 as a pulse/no pulse decision 44 and a step of resetting the timer within the demand controller 46 comprises substantially all of the timing logic employed by said devices.

Thus, by way of illustration and not limitation, the pacemaker controller 42 may comprise means for controlling arrhythmia and/or providing defibrillation. Reference may be had, e.g., to U.S. Pat. Nos. 6,278,897, 6,275,730 (method and apparatus for treating cardiac arrhythmia), 6,274,265 (implantable medical device), 6,272,380 apparatus for treating atrial tachy arrhythmias), 6,270,457, 6,266,566, 6,266,564, 6,266,563 (method and apparatus for treating cardiac arrhythmia), 6,266,555, 6,256,537 (pacemaker system with inhibition of AV node for rate regulation during atrial fibrillation), and the like. The entire disclosure of each of these United States patents is hereby incorporated by reference into this specification.

Referring again to FIG. 7, it may be seen that this invention preferably employs another layer of timing logic contained in pulsewidth controller 47. In this embodiment, pacemaker demand controller 43 provides programmatic input to said pulsewidth controller, said input including recent history of the patient's physiologic state, recent fluctuations in heart demand based upon exercise or other stress factors, and recent history of the voltages and pulsewidths used by controller 47 to pace the heart. A command from the pacemaker demand controller 43 based upon the decision in step 44 results in step 48, which is the initiation of a pulsewidth signal made up of a large number of micropulses; instructions regarding the pulse duration, spacing, and voltage level are sent to the pulsewidth controller 47 by pacemaker demand controller 43. Step 50 sends the first command to driver circuit 51, and also sends a synchronization signal to trigger decision step 60. If no heartbeat has been sensed, a counter 62 increments, and instructs the pulsewidth controller 47 to repeat step 50 and send another command to driver circuit 51 and another synchronization pulse to trigger decision step 60. This process is repeated until initiation of a heartbeat is sensed, resulting in decision step 60 sending a command 64 to end micropulse generation. Information regarding the number of micropulses required to initiate each heartbeat is sent back to the demand controller 43, which may modify its resident algorithm based upon programmed parameters. Demand controller 43 may also in turn communicate with the external programmer 40, depending upon preset parameters in order to either send an alert to the patient, or to initiate information exchange with the physician who may direct some change in the course of therapy based on said information. It should be noted again that while the statements made in describing the process depicted in FIG. 7 may imply fixed values of timing and voltage for the micropulses used to pace the heart, time periods 26 and 28 from FIG. 6 may range from below 1 microsecond to over 100 microseconds and may be variable over time, both in absolute duration and in their ratio. Further, the applied voltage 24 may be variable over time within a single pacing signal 20, or between pacing signals, as a function of changes in physiologic demand or based on changes in programmed response of the pacemaker system.

Referring once again to FIG. 7, upon command from the pulsewidth controller 47, driver circuit 51 creates an appropriate micropulse for delivery 52 to the heart. As will be apparent to those skilled in the art, one may use conventional pulsed signal generators as driver 51. Reference may be had, for example, to U.S. Pat. Nos. 4,012,641 (portable pulsed signal generator), 5,217,009 (compact biomedical pulsed signal generator), 6,011,994 (biomedical pulsed signal generator), and the like. The entire disclosure of this United States patent is hereby incorporated by reference into this specification. As will be apparent, the pulsed signal generator circuitry can produce variable outputs.

By way of further illustration, and referring to pages 14–29 et seq. of Donald G. Fink's "Electronics Engineers' Handbook," Second Edition (McGraw Hill Book Company, New York, N.Y., 1982), it will be seen that a high frequency signal made up of individual pulses, all of the same voltage, but having duty cycles less than 1.0, will produce an effective applied voltage equivalent to the duty cycle multiplied by the applied pulse voltage.

Referring again to FIG. 7, and for purposes of clarity in illustrating the utility of this invention, the pacemaker lead and electrodes 53 that send and receive energy from the heart 56 are described as parts 54A, 54B, 58A, and 58B. As shown in FIGS. 3, 4 and 5, and as described in the corresponding part of this specification, cardiac pacemaker lead 2, 102 or 202 may be an electrical conductor or may comprise one or more optical fibers that carry light energy between the pacemaker device case and the electrodes. The embodiment employing optical means is intended to create pacemaker leads that are immune to the intense radio frequency and magnetic fields associated with magnetic resonance imaging (MRI). Thus in FIG. 7, parts 54A and 58A are similar to traditional electrical pacemaker leads and electrodes, and parts 54B and 58B are comparable optical pacemaker leads that are specifically designed to be used in an MRI diagnostic environment. Further description in this specification will refer simply to parts 54 and 58.

Parts 54 and 58 are shown in FIG. 7 as being separate. In some pacemaker system designs, the pacing and sensing functions may be conducted via the same lead and electrodes; however for reasons of clarity they are shown herein as separate. A signal from the heart 56, indicating the initiation of a heartbeat, returns to the decision step 60, which in turn ends the micropulse pacing of the heart upon receipt of said signal.

Figure 8:
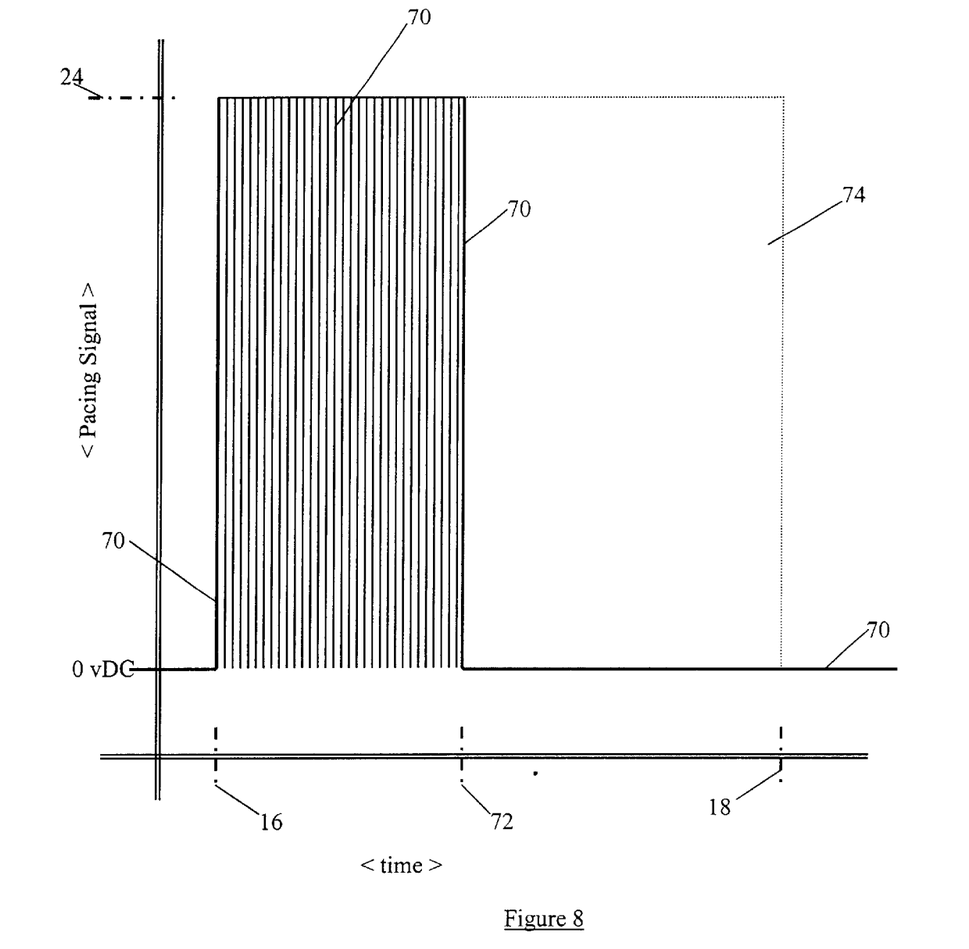
FIG. 8 is a graph depicting the operation of one preferred embodiment of this invention that gains energy efficiency by means of early termination of the pacing signal.

FIG. 8 is a graph depicting the operation of one preferred embodiment of this invention that gains energy efficiency by means of early termination of the pacing signal, but which uses a constant voltage applied to the micropulses comprising the pacing signal. The peak voltage of pulses that make up pacing signal 70 rises from zero to voltage 24 at time 16, as previously shown in FIG. 6. At time 72, when a signal from heart 56 causes cessation of the micropulsing process in step 64 in FIG. 7, the pulsewidth-pacing signal 70 returns to zero until the next pacing signal is commanded from the demand controller 43. The shaded area 74 depicts the additional signal that a traditional pacemaker not practicing this invention would send to pace the heart after the onset of a beat at time 72. As discussed previously, standard clinical practice calls for a threefold safety factor in pulse duration; thus this invention, employed in a manner depicted in FIG. 8, would result in up to approximately a 65 percent reduction in energy consumption for the pacemaker system.

Figure 9:
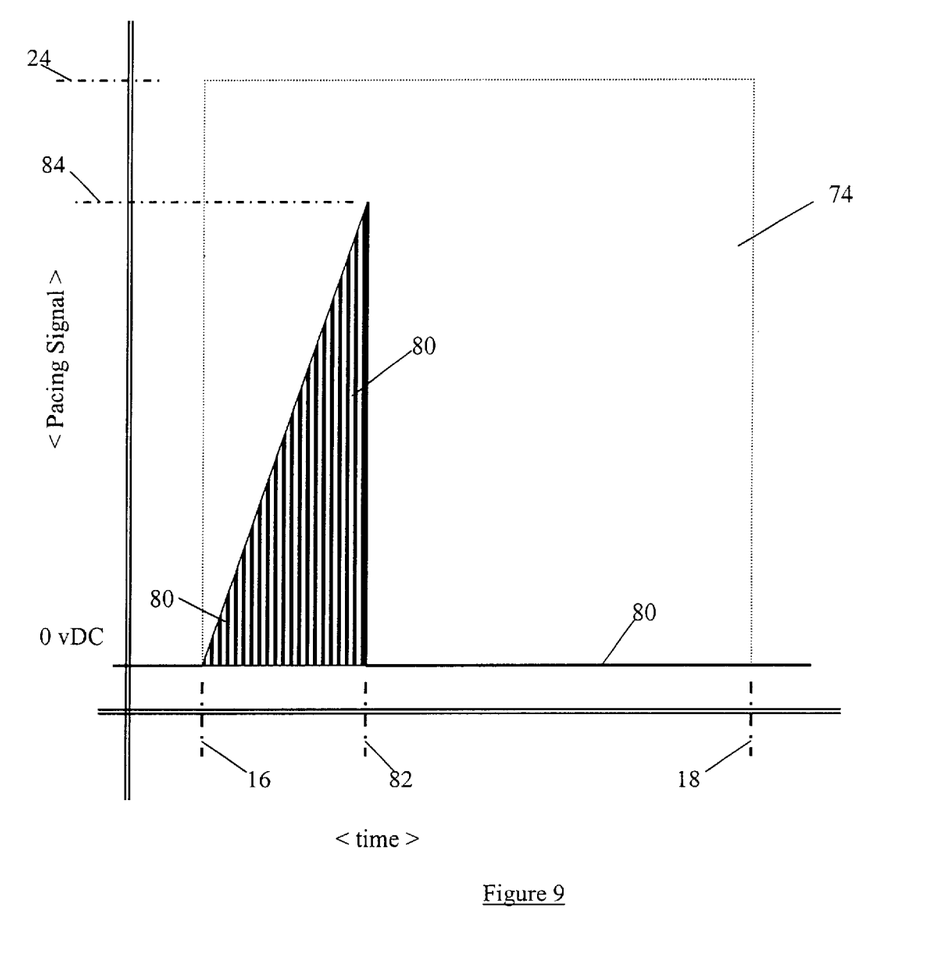
FIG. 9 is a graph depicting the operation of another preferred embodiment of this invention that gains energy efficiency by means of both early termination of the pacing signal and by gradient pulsewidth power control.

FIG. 9 is a graph depicting the operation of another preferred embodiment of this invention that gains energy efficiency by means of both early termination of the pacing signal and by the additional use of gradient pulsewidth power control. As in the previous embodiment, pulsewidth-pacing signal 80 begins to rise from zero at time 16, and the voltage of each of the micropulses rises with each micropulse cycle. FIG. 9 depicts a linear rise with time, but experimentation may result in a different algorithm that better matches the electrochemistry of cardiac tissue; thus FIG. 9 should be considered as illustrative of a variety of waveforms that may be employed to excite the heart. At time 82, when a signal from heart 56 causes cessation of the micropulsing process in step 64 in FIG. 7, the pulsewidth-pacing signal 80 returns to zero until the next pacing signal is commanded from the demand controller 43. As in the example of FIG. 8, the shaded area 74 depicts the signal that a traditional pacemaker not practicing this invention would send to pace the heart. As discussed previously, standard clinical practice calls for a threefold safety factor in pulse duration. The typical twofold safety factor in applied voltage results in a power level that is four times higher than the minimum to pace the specific patient's heart. Thus in combination the joint safety factors applied to voltage and pulse duration result in an energy utilization that is twelve times higher than the minimum needed to reliably pace that individual's heart. By practicing this invention, which permits the cessation of the pulse-width-pacing signal virtually the instant the heart begins to beat, the energy consumption of a pacemaker may be reduced by as much as 90%.

It should also be understood that in using a pulsewidth modulation control technique, it is not necessary to alter the actual peak voltage of the pulses that make up the pacing signal to effect an apparent change in applied voltage. If the frequency of the pulses is high enough in comparison to the response time of the circuit (in this case a circuit that comprises lead 102, electrodes 3 and 4, and the cardiac tissue through which the pacing signal is conducted, the tissue will react in the same manner as if the applied voltage were the actual peak voltage multiplied by the duty cycle. Thus the electronic circuit may be designed to utilize a single voltage and adjust duty cycle by adjusting the ratio of times 26 and 28. This permits optimization the energy efficiency of power sources and switching circuits.

Figure 10:
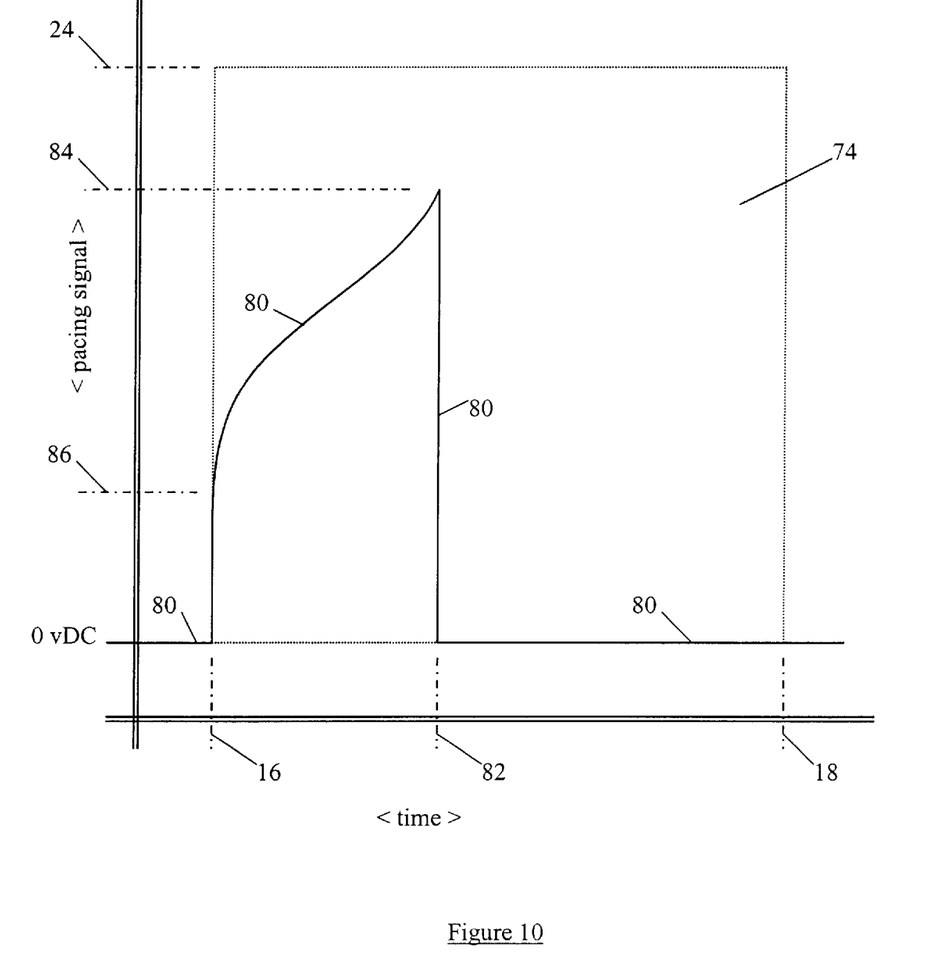
FIG. 10 is another graph of the embodiment in FIG. 9, but with alternate waveform of the pacing signal.

FIG. 10 depicts an alternative overall waveform for pacing signal 80. Note that for reasons of simplicity the overall value of peak voltage is shown for pacing signal 80, and not the individual pulse-widths, as shown in FIG. 9. However, this embodiment still makes use of the high-frequency pulsewidth approach shown in greater detail in FIGS. 8 and 9. Whereas FIG. 9 depicts a linear rise with time, FIG. 10 depicts an initial rise of pacing signal 80 at time 16 from 0 vDC to voltage 86, followed by a non-linear increase to voltage 84, at which time 82 a heartbeat has been sensed, and pacing signal 80 is cut off as in the previous embodiments described herein. Experimentation may result in a different algorithm that better matches the electrochemistry of cardiac tissue, and this algorithm may be developed for the specific patient during the initial post-implantation period. Thus FIGS. 9 and 10 should be considered as illustrative of a variety of waveforms that may be employed to excite the heart, and may be made specific to the needs of each pacemaker patient.

As in the previous embodiment depicted in FIG. 9, the use of pulsewidth modulation techniques in the embodiment depicted in FIG. 10 permits optimization of energy efficiency by adjusting duty cycle rather than adjusting actual peak voltage.

Referring again to the text "Cardiac Pacing for the Clinician," and specifically to FIG. 1.15 on page 22, it may be seen that the stimulation threshold of the heart increases substantially after initial implantation and use. It is generally acknowledged that damage to sensitive cardiac tissues is one of the primary causes of this increase, which in requires higher pacing voltages and safety factors. By practicing this invention, thus substantially reducing the energy applied to sensitive cardiac tissues, increases in stimulation threshold may be substantially reduced.

Referring yet again to the text "Cardiac Pacing for the Clinician," and specifically to the discussion of the polarization effect at the electrode on pages 5 and 6, it may further be seen that by using substantially lower power level and pulse duration to pace the heart, the effects of polarization potential will be reduced; this reduces the effective impedance of cardiac tissue at the tissue/electrode interface, and reduces the background potential that interferes with sensitive measurements of cardiac tissue activity.

In one preferred embodiment of this invention, there is provided a cardiac assist system comprising means for delivering a first pacing pulse from said system to a heart, means for ceasing the delivery of said first pacing pulse to said heart, means for sensing whether said heart is beating, and means for delivering a second pacing pulse from said system to said heart, wherein: (a) said first pacing pulse and said second pacing pulse are delivered to said heart within a period of less than about 100 milliseconds, and wherein each of said first pacing pulse and said second pacing pulse has a voltage of from about 2 to about 5 volts direct current, and the time between said delivery of said first pacing pulse and said second pacing pulse is at least about 1 microsecond, (b) said first pacing pulse and said second pacing pulse are delivered to said heart at a frequency of from about 2 kilohertz to about 5 megahertz, (c) said first pacing pulse and said second pacing pulse each have a duration of from about 0.1 microseconds to about 500 milliseconds, and (d) said cardiac assist system is comprised of means for varying at least one property of a pacing pulse selected from the group consisting of said first pacing pulse, said second pacing pulse, and both said first pacing pulse and said second pacing pulse.

In this embodiment, the first pacing pulse and the second pacing pulse are preferably delivered to the heart in a period of less than 5 milliseconds and, more preferably, in a period of less than 1 millisecond.

In this embodiment, each of the first pacing pulse and the second pacing pulse preferably has a voltage of from about 2 to about 3 volts.

In this embodiment, the time between delivery of the first pacing pulse and the second pacing pulse preferably does not exceed about 0.5 times the duration of the first or the second pacing pulses.

In one aspect of this embodiment, a multiplicity of such pacing pulses are preferably delivered to the heart at a frequency of from about 2,000 to 4,000 hertz; in this aspect, from about 2 to about 4 such pulses are delivered for each pulsing signal.

In another aspect of this embodiment, a multiplicity of such pacing pulses are preferably delivered to the heart at a frequency of from about 100 to 400 kilohertz; in this aspect, from about 50 to about 500 such pulses are delivered for each pulsing signal.

In this embodiment, each of the first pacing pulse and the second pacing pulse preferably have a duration which is often determined solely by its frequency, in the case of a 100 percent duty cycle. In one aspect, such duration is from about 100 to about 400 microseconds. In another aspect, such duration is from about 1 to about 10 microseconds.

In this embodiment, the cardiac assist system is comprised of means for varying at least one of the properties of the first pacing pulse, the second pacing pulse, and/or one more of the other pacing pulses. The properties so varied may include, e.g., the voltage, the duration, frequency, the number, the shape, etc. of the pacing pulses. By means of conventional feedback loops (see, e.g. FIG. 7 and its corresponding discussion), the optimal frequency and/or duration and/or intensity and/or energy and/or other property or properties of pacing signal necessary for the heart at any particular point in time may be iteratively derived by conventional software means.

In another embodiment, there is provided a cardiac assist system which comprises means for creating a pulsewidth-modulated cardiac pacing signal, means for sensing cardiac activity during dwell periods between micropulses in said pacing signal, and means for terminating said pacing signal upon initiation of heart beat.

This cardiac assist system may optionally comprise means for isolating sensing electrodes from polarization potential generated by cardiac tissue as a result of pacing signals.

In one aspect of this cardiac assist system, the pulsewidth-modulated cardiac pacing signal employs individual micropulses having variable voltage between about 1 volts direct current and 5 volts direct current.

In another aspect of this cardiac assist system, the pulsewidth-modulated cardiac pacing signal employs individual micropulses having variable duration between about 1 microsecond and 100 microseconds.

In yet another aspect of this cardiac assist system, the system communicates with an external device to report status, to report alerts, and to accept instructions for modifications to its control algorithm.

It is to be understood that the aforementioned description is illustrative only and that changes can be made in the apparatus, in the sequence and combinations of process steps, as well as in other aspects of the invention discussed herein, without departing from the scope of the invention as defined in the following claims.

I claim:

1. A cardiac assist system comprising means for delivering a first pacing pulse from said system to a heart, means for ceasing the delivery of said first pacing pulse to said heart, means for sensing whether said heart is beating, and means for delivering a second pacing pulse from said system to said heart, wherein:
   (a) said first pacing pulse and said second pacing pulse are delivered to said heart within a period of less than about 100 milliseconds, wherein:
      1. each of said first pacing pulse and said second pacing pulse has a voltage of from about 2 to about 5 volts direct current,
      2. a time between said delivery of said first pacing pulse and said second pacing pulse is at least about 1 microsecond,
   (b) said first pacing pulse and said second pacing pulse are delivered to said heart at a frequency of from about 2 kilohertz to about 5 megahertz,
   (c) said first pacing pulse and said second pacing pulse each have a duration of from about 0.1 microseconds to about 500 milliseconds, and
   (d) said cardiac assist system is comprised of means for varying at least one property of a pacing pulse selected from the group consisting of said first pacing pulse, said second pacing pulse, and both said first pacing pulse and said second pacing pulse.

2. The cardiac assist system as recited in claim 1, wherein said cardiac assist system comprises a first sensing electrode and a second sensing electrode.

3. The cardiac assist system as recited in claim 2, wherein said cardiac assist system comprises a first pacing electrode and second pacing electrode.

4. The cardiac assist system as recited in claim 3, wherein each of said first sensing electrode and said second sensing electrode is disposed at a distance of at least about 5 millimeters from each of said first pacing electrode and said second pacing electrode.

5. The cardiac assist system as recited in claim 1, wherein said time between said delivery of said first pacing pulse and said second pacing pulse is from about 1 microsecond to about 100 microseconds.

6. The cardiac assist system as recited in claim 1, wherein said cardiac assist system is adapted to be disposed within a biological organism.

7. The cardiac assist system as recited in claim 1, further comprising a first receiver for receiving information.

8. The cardiac assist system as recited in claim 7, wherein said receiver is a first transceiver.

9. The cardiac assist system as recited in claim 8, wherein said cardiac assist system is comprised of a second transceiver.

10. The cardiac assist system as recited in claim 9, wherein said second transceiver is operatively connected to said means for delivering a first pacing pulse from said system to said heart, and to said means for delivering a second pacing pulse from said system to said heart.

11. The cardiac assist system as recited in claim 1, wherein said cardiac assist system further comprises a defibrillator.

12. The cardiac assist system as recited in claim 1, wherein said cardiac assist system is comprised of means for controlling cardiac arrhythmia.

13. The cardiac assist system as recited in claim 1, wherein said means for delivering a first pacing pulse from said system to said heart is a variable means for delivering a variable pacing signal from said system to said heart.

14. The cardiac assist system as recited in claim 1, wherein said means for delivering a second pacing pulse from said system to said heart is a variable means for delivering a variable pacing signal from said system to said heart.

* * * * *